Feb. 8, 1955 E. PRUSHEK Plant Pat. 1,348
CHRYSANTHEMUM PLANT
Filed March 5, 1954
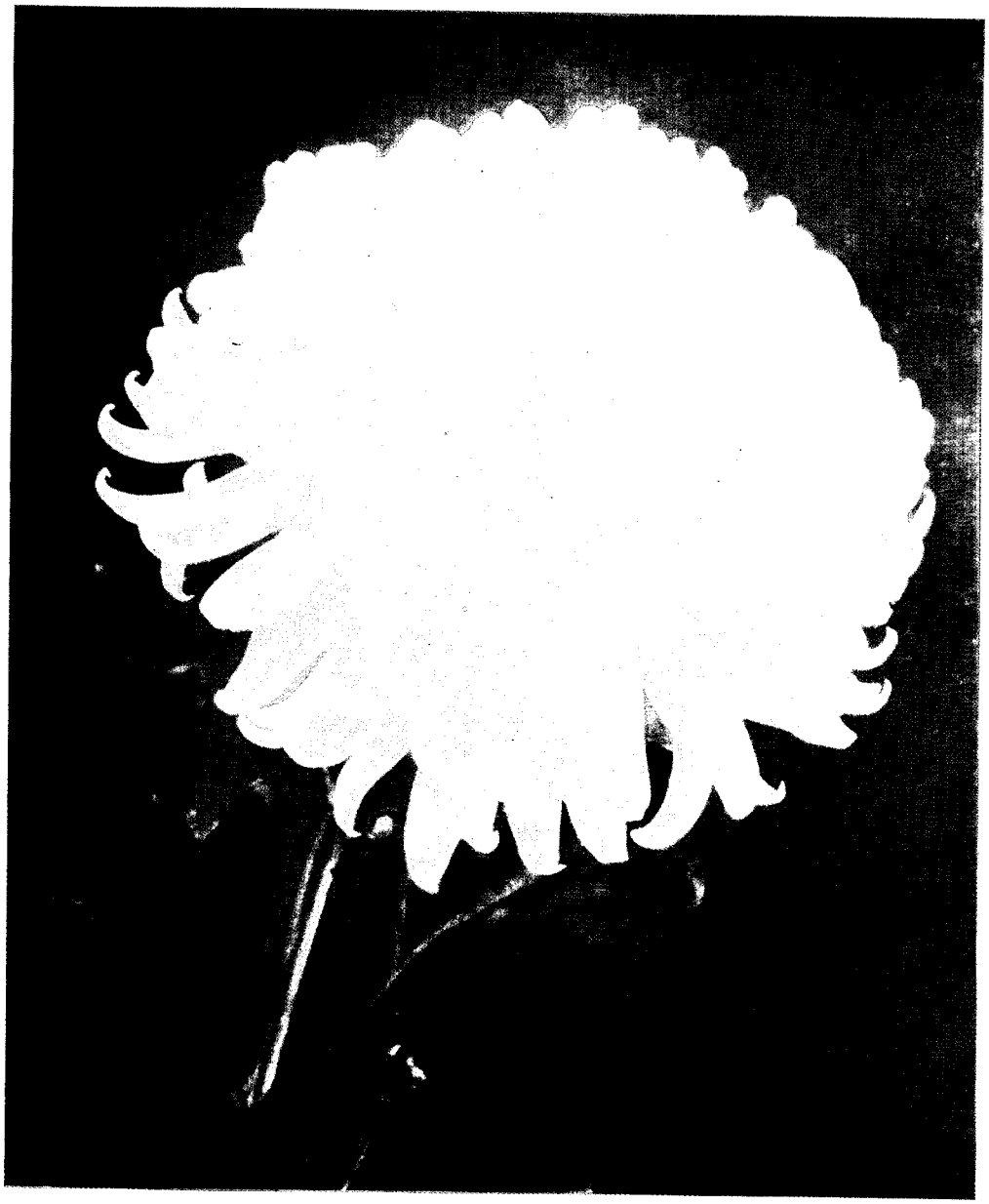
Inventor
Emil Prushek
By: Robert Cobb
Attorneys United States Patent Office Plant Pat. 1,348
Patented Feb. 8, 1955

1,348

CHRYSANTHEMUM PLANT

Emil Prushek, Niles, Mich., assignor to Inter-State Nurseries, Inc., Hamburg, Iowa, a corporation of Delaware Application March 5, 1954, Serial No. 414,530

1 Claim. (Cl. 47—60)

The present invention relates to a new and distinct variety of chrysanthemum plant of the incurved type, which was originated by me by crossing two unnamed and unpatented seedlings which are identified in my breeding records as Seedling #3498 and #3468, respectively.

The primary objectives of this breeding was to produce a new and improved variety of chrysanthemum of the incurved type which does not require pruning or bud removal in order to produce blooms of large size and good quality. A still further objective was to produce an improved chrysanthemum of the aforementioned type and at the same time one which combines the characteristics of early and free-blooming habit, and the production of distinctive, highly attractive and relatively large blooms. These objectives were fully achieved. The blooms of my new variety are quite large, fully incurved, and have a rich Golden Yellow general color tonality. It is an early bloomer, and commences blooming by late August or early in September, thereby enhancing its garden value, which value is still further benefitted by its extremely free-blooming habit. My new variety will actually produce many dozens of blooms even if the side blooms are not disbudded, and the center flower is usually very large without resorting to any pruning or disbudding.

The foregoing characteristics definitely distinguish my new variety from its parents, as well as from all other varieties of its class, and asexual reproduction of my new variety of soft-wood top cuttings of the spring growth, as performed at Niles, Michigan, shows that the aforesaid characteristics and distinctions come true to form and are established and transmitted through succeeding propagations.

The accompanying drawing shows a typical specimen bloom and some of the foliage of my new variety as depicted in color as nearly true as it is reasonably possible to make the same in a color illustration of this character.

The following is a detailed description of my new variety, as grown and observed at Niles, Michigan, with color terminology in accordance with Robert F. Wilson's Horticultural Colour Chart, except where general color terms of ordinary dictionary significance are obvious:

Parentage: An unnamed seedling identified as #3498 × an unnamed seedling identified as #3468.
Classification: *Chrysanthemum hortorum.*
Type: Incurved.
Growth: Medium vigor; open, somewhat spreading.
Flower borne: Usually only one flower on each of many long stems; as each large bloom is cut, a succession of equally large blooms follows and continues through the longest season of any known variety.
Cold resistance: Average, as compared with other varieties grown under comparable cultural conditions at Niles, Michigan.
Blooming period: Opens with the earliest varieties and continues to the end of the growing season with the late varieties; beginning late August and continuing to November, depending upon freezing weather; longest blooming period of any known variety.
Bud:
*Color.* — When sepals first divide—Light Yellow. When petals begin to unfurl—Aureolin, Plate 3. When half blown: inside of petals—Aureolin, Plate 3; reverse of petals—Aureolin, Plate 3.
*Peduncle.* — Color — Medium Green. Strength—medium.
Bloom:
*Size.*—Large; from 4 to 5 inches.
*Stems.*—Long; rather slender.
*Form.*—Incurved.
*Petalage.*—Many petals.
*Color.* — Center of flower — uniformly Aureolin, Plate 3. Outer petals — unusually uniformly Aureolin, Plate 3, but some petals shaded a little deeper. Base of petals—Aureolin, Plate 3. Inside of petals—Aureolin, Plate 3. Reverse of petals—Aureolin, Plate 3.
*General color tonality.*—Aureolin, Plate 3.
*Petals.*—Texture—firm. Form—incurved.
*Fragrance.*—Typical chrysanthemum fragrance.
Plant:
*Form.*—Spreading.
*Growth.*—Medium.
*Foliage.*—Size—from 2 to 2½ inches. Quantity—average. Color: upper side—Dark Green; reverse side—Light Green. Texture—firm.

I claim:

A new and distinct variety of chrysanthemum plant of the incurved type, substantially as herein shown and described, characterized particularly as to novelty by its freedom and floriferousness of bloom, by its habit of bearing relatively large blooms usually singly or relatively long stems without requiring pruning or disbudding, by the distinctive, rich Golden Yellow general color tonality of its bloom, and by its early and unusually prolonged blooming habit.

No references cited.